(12) United States Patent
Clement et al.

(10) Patent No.: US 8,658,826 B2
(45) Date of Patent: Feb. 25, 2014

(54) AMINO ACID DERIVATIVES USED AS PHARMACEUTICAL SUBSTANCES

(75) Inventors: Bernd Clement, Kiel (DE); Christiane Wolter-Reeh, Holm (DE); Helen Schenk, Hamburg (DE)

(73) Assignee: Dritte Patentportfolio Beteiligungsgesellschaft mgH & Co. KG, Schönefeld/Waltersdorf (DE)

( * ) Notice: Subject to any disclaimer, the term of this patent is extended or adjusted under 35 U.S.C. 154(b) by 341 days.

(21) Appl. No.: 12/847,544

(22) Filed: Jul. 30, 2010

(65) Prior Publication Data
US 2011/0021835 A1     Jan. 27, 2011

Related U.S. Application Data

(63) Continuation of application No. PCT/EP2009/051162, filed on Feb. 2, 2009.

(30) Foreign Application Priority Data

Feb. 1, 2008 (DE) .......................... 10 2008 007 440

(51) Int. Cl.
*C07C 257/00* (2006.01)

(52) U.S. Cl.
USPC .......................................................... 564/244

(58) Field of Classification Search
None
See application file for complete search history.

(56) References Cited

U.S. PATENT DOCUMENTS 5,786,383 A     7/1998     Clement
7,608,623 B2    10/2009    Sperl et al.

FOREIGN PATENT DOCUMENTS

| DE | 43 21 444 A1 | 1/1995 |
|----|--------------|--------|
| DE | 103 23 898 A1 | 12/2004 |
| WO | 98/57932 A1 | 12/1998 |
| WO | 01/97794 A2 | 12/2001 |

OTHER PUBLICATIONS

Database CAPLUS Chemical Abstracts Service, Columbus, Ohio, US; Database Accession No. 1999:9815, Abstract of Kalrsson et al., WO 9857932 (1998).*
Database CAPLUS Chemical Abstracts Service, Columbus, Ohio, US; Database Accession No. 2006:31454, Abstract of Hayashi et al., WO 2006003881 (2006).*
Database CAPLUS Chemical Abstracts Service, Columbus, Ohio, US; Database Accession No. 2006:103275, Abstract of Hayashi et al., WO 2006011499 (2006).*
Translation of Int'l Preliminary Report of Patentability issued on Jun. 8, 2010 in Int'l Application No. PCT/EP2009/051162.
Office Action Issued Oct. 2, 2008 in German Appln. Ser. No. 10 2008 007 440.3.
Office Action issued Dec. 7, 2011 in CN Application No. 200980103402.1.
Notice of Third Party Submission issued Feb. 14, 2012 in EP Application No. 09706232.7.

(Continued)

*Primary Examiner* — Karl J Puttlitz
(74) *Attorney, Agent, or Firm* — Panitch Schwarze Belisario & Nadel LLP

(57) ABSTRACT

The invention relates to a method for improving bioavailability of pharmaceutical substances and for allowing the pharmaceutical substances to permeate the blood-brain barrier, the pharmaceutical substances having at least one or more amidine, guanidine, N-hydroxyamidine (amidoxime) or N-hydroxyguanidine functions. The invention also relates to medicaments containing the correspondingly modified pharmaceutical substances.

10 Claims, 3 Drawing Sheets

(56) References Cited

OTHER PUBLICATIONS

Clement, B. et al., "Diacetyldiamidoximeester of pentamidine, a prodrug for treatment of protozoal diseases: synthesis, in vitro and in vivo biotransformation", ChemMedChem, vol. 1, pp. 1260-1267 (2006).

Li, W. et al., "Indentification of GS 4104 as an orally bioavailable prodrug of the influenza virus neuraminidase inhibitor GS 4071", Antimicrobial Agents and Chemotherapy, vol. 42, No. 3, pp. 647-653, Mar. 1998.

Lain-Yen Hu, et al., "Synthesis and structure-activity studies of N-(1-naphthyl)-N'-(3-ethylphenyl)-N'-methylguanidine analogs (CNS 1102 analogs) for NMDA-ion-channel blockage", American Cancer Society, Abstracts of Paper, At The National Meeting, American Chemical Society, vol. 206, No. 1-2, Jan. 1, 1993.

Int'l Search Report issued on Oct. 6, 2009 in Int'l Application No. PCT/EP2009/051162.

Written Opinion issued on Oct. 6, 2009 in Int'l Application No. PCT/EP2009/051162.

English Translation of Response to Written Opinion on Dec. 28, 2009 in Int'l Application No. PCT/EP2009/051162.

Int'l Preliminary Examination Report issued on Jun. 8, 2010 in Int'l Application No. PCT/EP2009/051162.

* cited by examiner

AMINO ACID DERIVATIVES USED AS PHARMACEUTICAL SUBSTANCES

CROSS-REFERENCE TO RELATED APPLICATIONS

This application is a Continuation of International Application No. PCT/EP2009/051162, filed Feb. 2, 2009, which was published in the German language on Aug. 6, 2009, under International Publication No. WO 2009/095503 A2 and the disclosure of which is incorporated herein by reference.

FIELD OF THE INVENTION

The present invention relates to the use of an amidoxime amino acid ester in a method for improving the bioavailability and enabling the blood-brain barrier crossing of medicinal substances, which have at least one or more amidine functions, guanidine functions, N-hydroxyamidine (amidoxime) functions or N-hydroxyguanidine functions, and drugs containing correspondingly modified medicinal substances.

BACKGROUND OF THE INVENTION

N-hydroxyamidines (amidoximes) and N-hydroxyguanidines represent known prodrug principles for increasing the oral bioavailability of amidines [Clement, B. Methoden zur Behandlung und Prophylaxe der *Pneumocystis carinii* Pneumonie (PCP) und anderen Erkrankungen sowie Verbindungen und Formulierungen zum Gebrauch bei besagten Methoden, P 432-444.4, 1993] and guanidines.

Pharmaceutical preparations containing an active agent having one or more amidine or guanidine functions exhibit almost no pharmacological effect in oral application. The precondition for a therapeutical effect of an active agent after oral administration is represented by its resorption from the gastrointestinal tract. The most important mechanism of such an effect is passive diffusion. The degree of resorption by way of passive diffusion is dependent on the lipophilicity and thus also the acidity and basicity of the active agent.

Highly basic compounds such as amidines and guanidines are present in the stomach (pH 1) and small intestine (pH 6.4) in an almost completely protonated form. A resorption after oral administration, which requires the passing of lipid bilayers of the membranes of the gastrointestinal tract, therefore only occurs to a very low degree.

Another problem in the medication of many diseases is the necessity to cross the blood-brain barrier. The blood-brain barrier is an effective barrier with regard to the resorption of substances into the brain. It ensures the selective uptake and prevents the penetration of substances. Furthermore, the blood-brain barrier does no only act as a physical but also as an enzymatic barrier. Various processes are involved in the penetration of substances into the brain. As compared to other indications, only few drugs are marketed, which develop their effect in the central nervous system (CNS). The greater part thereof reaches the CNS by diffusion. Diseases like epilepsy, chronic pain or depressions are treated this way. Other serious functional disorders such as brain tumors or amyotrophic lateral sclerosis yet cannot be treated in this way today [PARDRIDGE, W. M. *NeuroRx* 2005, 2, 3-14]. For being able to cross the blood-brain barrier by way of passive diffusion, a substance is required to be lipophilic, have a lower molecular weight than 400-500 Da, and be present in an uncharged state. For resorbing specifically small molecules such as glucose or amino acids, various transporter systems such as nucleoside transporters, influx and efflux transporters for organic anions, glucose transporters, peptide transporters, and amino acid transporters are expressed on the blood-brain barrier [TAMAI, I.; TSUJI, A. *J. Pharm Sci* 2000, 89, 1371-1388 and DE BOER, A.; VAN DER SANDT, I. *Annu Rev Pharmacol Toxicol* 2003, 43, 629-656]. Larger molecules such as insulin or iron-containing transferrin are resorbed via the receptor-mediated transport. In this case, the insulin and transferrin receptors particularly play an important role [DE BOER, A.; VAN DER SANDT, I. *Annu Rev Phamacol Toxicol* 2003, 43, 629-656; PARDRIDGE, W. M. *Mol Interv* 2003, 3, 90-105]. Taking the amino acid L-dopa as an example, one has used a prodrug principle for the water-soluble catecholamine dopamine to be capable of passing the blood-brain barrier. The transport is performed by the amino acid transporter LAT1 (large neutral amino acid transporter). After the passage, the decarboxylation into dopamine takes place [PARDRIDGE, W. M. *Mol Interv* 2003, 3, 90-105].

Diamidines are used as antiparasitic agents against malaria, *pneumocystis jiroveci* (previously *carinii*) pneumonia, trypanosomiasis (African sleeping sickness), and leishmaniasis [WERBOVETZ, K. *Curr Opin Investig Drugs* 2006, 7, 147-157]. Particularly in developing countries, these diseases represent a serious problem involving high mortality rates.

Three diamidines to be applied parenterally are on the market. Pentamidine (Pentacarinat®) has been used in the early stage of the African sleeping sickness already for 60 years. Efficiency is no longer provided in the $2^{nd}$ stage of the African sleeping sickness, the meningo-encephalitic stage, since the blood-brain barrier cannot be passed successfully. As a result, highly toxic arsenic compounds must be administered. There is a lack of medicinal substances which are efficient in the $2^{nd}$ stage of the African sleeping sickness.

It is likely that all of the active agents, which have an amidine or a guanidine as a functional group, exhibit an insufficient resorption in the oral application, if they can only be resorbed by passive diffusion.

The N-hydroxylated derivatives such as amidoximes, and the N-hydroxyguanidines, due to the introduction of the oxygen atom, exhibit a lower basicity. Under physiological conditions, they are not present in a protonated form. Benzamidoxime represents a model compound for many medicinal substances containing an amidoxime function [Clement, B., *Drug Met Rev* 2002, 34, 565-579].

Pentamidine and diminazene represent diamidines and are not resorbed after oral application. They were therefore transferred into amidoxime prodrugs. (DE 10 2006 034 256.9).

The example pentamidine demonstrates that the transfer into the pentoxime ester also entails a reduction of the solubility. This probably is also the reason for the bioavailability of pentamidine not to reach one hundred percent after oral application of the pentoxime ester [Clement, B.; Bürenheide, A.; Rieckert, W.; Schwarz, J., *ChemMedChem* 2006, 1, 1260-7].

Furthermore, the reduced water solubility induces the disadvantage that an administration of the medicinal substance is no longer possible by injecting aqueous solutions. This is a problem, particularly when an oral administration is out of question.

It is therefore the task of the present invention to increase the water solubility and thus also the oral bioavailability of substances, which had been transferred into amidoxime prodrugs or N-hydroxyguanidine prodrugs, and/or thus to enable the passing of the blood-brain barrier.

The task is solved by methods according to embodiments of the invention, such as those methods having the features of the independent claim, and those methods having the additional features of the dependent claims, which indicate advantageous arrangements of the invention.

BRIEF SUMMARY OF THE INVENTION

In one general aspect, the present invention relates to a method comprising using a partial structure forming formula (I), formula (II) or formula (III),

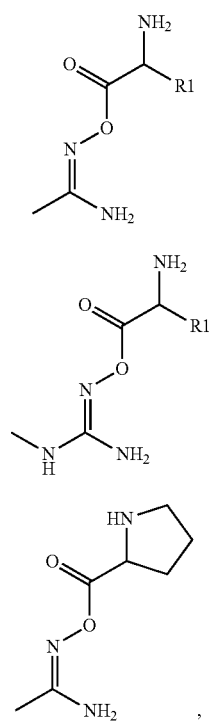

as a constituent of the overall structure of a prodrug for a medicinal substance, wherein R1 is selected from the group consisting of hydrogen, an alkyl radical, an aryl radical, and one selected from the group consisting of the following:

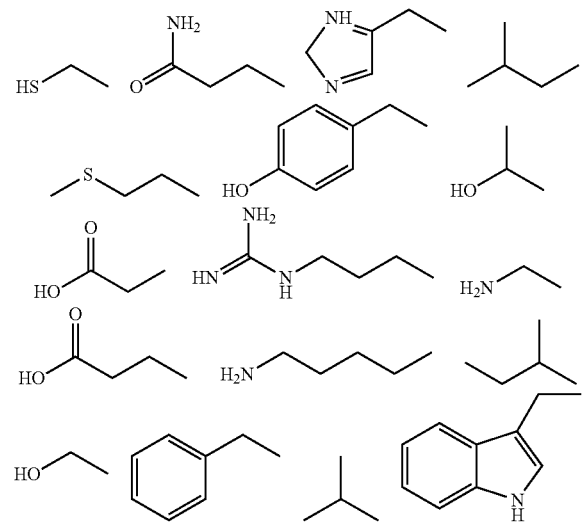

and the salts thereof.

A method according to an embodiment of the present invention comprises using an amidoxime amino acid ester of the formula (I), an N-hydroxyguanidine amino acid ester of the formula (II) or an amidoxime prolinyl ester of the formula (III), wherein R1 is selected from the group consisting of hydrogen, an alkyl radical, an aryl radical, and one selected from the group consisting of the following:

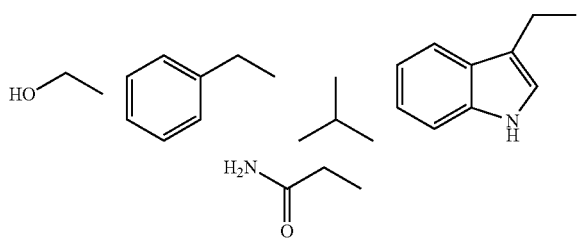

and the salts thereof, as a substitute for one or more amidine functions, N-hydroxyamidine (amidoxime) functions, guanidine functions or N-hydroxyguanidine functions of a prodrug for a medicinal substance for improving the solubility, bioavailability and/or capacity of the medicinal substance to pass the blood-brain barrier.

Another general aspect of the present invention relates to a prodrug comprising a partial structure having the formula (I), (II) or (III),

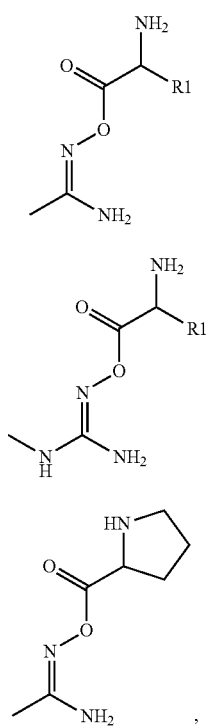

wherein R1 is selected from the group consisting of hydrogen, an alkyl radical, an aryl radical, and one selected from the group consisting of the following:

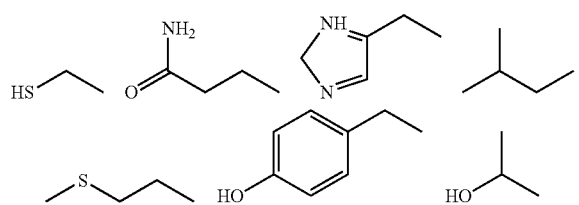

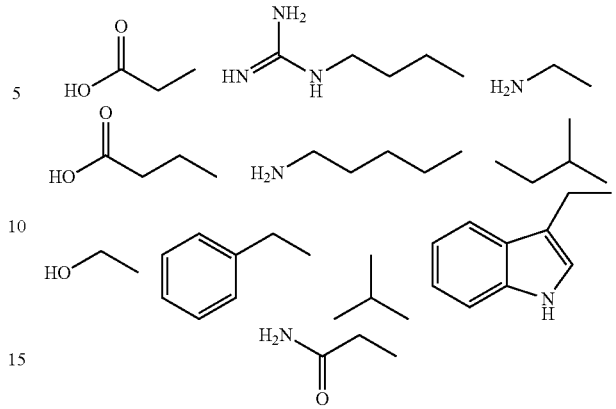

and the salts thereof, the prodrug is a prodrug for a medicinal substance, the medicinal substance is selected from the group consisting of protease inhibitors, DNA-intercalating compounds, RNA-intercalating compounds, inhibitors of viral enzymes and N-methyl-D-aspartate receptor antagonists.

In an embodiment of the present invention, the protease inhibitor is a thrombin inhibitor, an inhibitor of factor Xa, Factor VII or all of the proteases of the coagulation cascade, or a matriptase inhibitor.

In another embodiment of the present invention, the DNA-intercalating compound or RNA-intercalating compound is pentamidine, diminazene or isometamidium.

In yet another embodiment of the present invention, the inhibitor of viral enzymes is a neuraminidase inhibitor.

According to an embodiment of the present invention, the medicinal substance is configured for the prophylaxis and therapy of visceral and/or cutaneous leishmaniasis, trypanosomiasis, the $2^{nd}$ phase of trypanosomiasis, or pneumonia caused by *pneumocystis carinii*, for inhibiting the growth of malign tumors, for inhibiting blood coagulation, for blood pressure reduction, for neuroprotection, and for combating viral infections including influenza and HIV infections.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
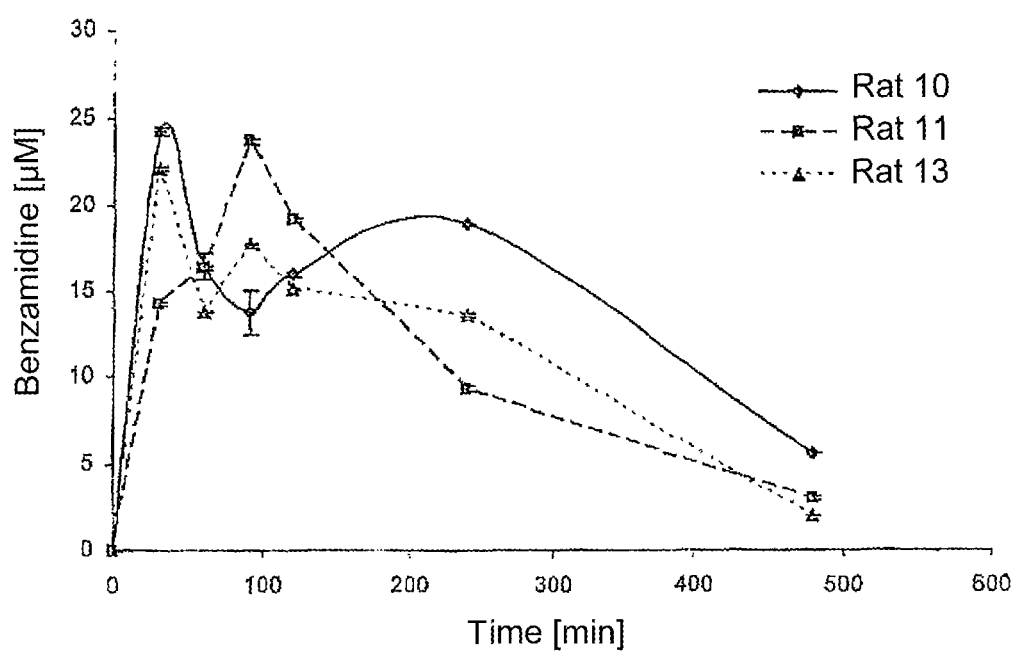
FIG. 1 is a graphic representation of the plasma levels of benzamidine in rats after the oral application of valbenzamidoxime.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

According to embodiments of the invention, amidoxime amino acid esters (I), N-hydroxyguanidine amino acid esters (II) or amidoxime prolinyl esters of the formula (III) are proposed to be used:

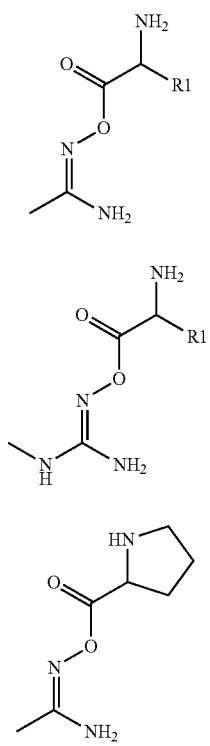

wherein R1 is hydrogen, an alkyl radical, an aryl radical, one of the groups listed in the following

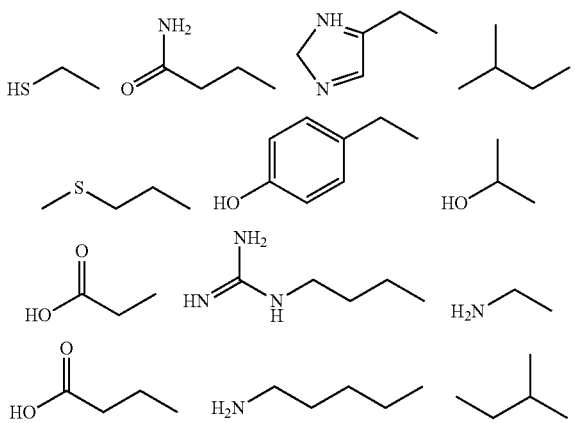

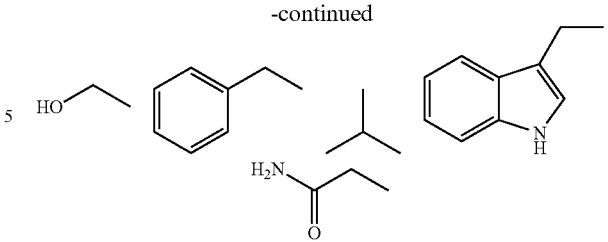

or the salts thereof, as a substitute for one or more amidine functions, N-hydroxyamidine (amidoxime) functions, guanidine functions or N-hydroxyguanidine functions of a medicinal substance in drugs for improving the solubility, bioavailability and enabling the medicinal substance to pass the blood-brain barrier.

N-hydroxyamidines (amidoximes) and N-hydroxyguanidines are successful prodrug principles for increasing the oral bioavailability of amidines (DE 10 2006 034 256.9).

The esterification of the amidoximes or N-hydroxyguanidines with amino acids proposed according to the invention, considerably improves the solubility, in particular the solubility in aqueous media, and the bioavailability as compared to known prodrugs. The particular advantage of the water-soluble amino acid esters according to the invention is their improved resorption from the gastrointestinal tract by specific amino acid and peptide transporters. A further advantage resides in the fact that, due to the esterification of the amidoximes or N-hydroxyguanidines with amino acids, injectable dosage forms are possible again, since the water solubility is restored just as in the case of amidines. The novel prodrug principles according to the invention provide the possibility of passing the blood-brain barrier. This would be a decisive progress in the therapy of the African sleeping sickness, since the $2^{nd}$ phase of the disease can thus also be treated efficiently.

According to the use according to the invention, the substituting of at least one or more amidine functions, N-hydroxyamidine (amidoxime) functions, guanidine functions or N-hydroxyguanidine functions by the amidoxime amino acid ester and N-hydroxyguanidine amino acid ester achieves for the solubility of the medicinal substance concerned to be increased. As a result, it can be firstly resorbed effectively after oral administration, and subsequently be reconverted again into the actual active form, the amidine, respectively, guanidine, by the body's own reductases and N-reductases (prodrug principle). The excellent resorbability of the modified amidoxime function or N-hydroxyguanidine function in the gastrointestinal tract is obviously due to the increased solubility of the active agent molecules. Furthermore, the novel prodrug principles are capable of enabling the blood-brain barrier to be overcome.

It is sufficient for the active agent to contain at least one or more active amidine functions, N-hydroxyamidine (amidoxime) functions, guanidine functions or N-hydroxyguanidine functions in the proposed form. The active agent consequently may contain, e.g., a plurality of amidoxime functions (e.g. two as in the case of pentoxime ester) or N-hydroxyguanidine functions, with at least one of these groups being then modified in the manner described above. Mixtures of active agents may be used just the same, provided that at least one active agent has one or more amidine functions, N-hydroxyamidine (amidoxime) functions, guanidine functions or N-hydroxyguanidine functions. The oral dosage form may be a liquid, semisolid or solid preparation, packaged in particular as a tablet, dragee, pellet or microcapsule. In this case, the active agent or active agent mixture for embodiments of this type, in which liquid preparations are used, is incorporated in a suitable non-toxic solvent such as water, monovalent alcohols, in particular ethanols, polyvalent alcohols, in particular glycerine and/or propanediol, polyglycols, in particular polyethylene glycols and/or miglyol, glycerol formal, dimethyl isosorbite, natural or synthetic oils. For producing semisolid or solid preparations, the usual base materials are used such as bentonite, veegum, guar flour and/or cellulose derivatives, in particular methylcellulose and/or carboxymethyl cellulose, as well as polymers of vinyl alcohols and/or vinylpyrrolidones, alginates, pectins, polyacrylates, solid and/or liquid polyethylene glycols, paraffins, fatty alcohols, vaselines and/or waxes, fatty acids and/or fatty acid esters.

Moreover, in solid preparations, the extenders known per se, such as colloidal silicic acid, talc, lactose, starch powder, sugar, gelatine, metal oxides and/or metal salts may be contained. Stabilizers, emulsifiers, deflocculants and preservatives are suitable as further additives.

The medicinal substances modified according to the use according to the invention exhibit an excellent resorbability and thus bioavailability in oral administration, whereby the pharmacological effect of the amidine or guanidine is distinctly increased. As a result, an optimum dosage form for the oral application of amidines may be provided.

The use according to the invention gains particular importance in that the functional groups amidine and guanidine are essential constituents of various important active agents for different fields of application. Inter alia, they are a constituent of the following substance classes, respectively active agents: protease inhibitors (thrombin inhibitors such as Melagatran, inhibitors of factor Xa, Factor VII, respectively of all of the proteases of the coagulation cascade; matriptase inhibitors), anticoagulants, thrombolytics, antifibrinolytics, DNA-intercalating and RNA-intercalating compounds (such as pentamidine, diminazene, isometamidium), N-methyl-D-aspartate receptor antagonists and inhibitors of viral enzymes (such as, e.g., neuraminidase inhibitors).

Active agents containing an effective amidine function or guanidine function may be used inter alia for inhibiting blood coagulation, for the prophylaxis and therapy of visceral and cutaneous leishmaniasis, trypanosomiasis (African sleeping sickness), pneumonia caused by *pneumocystis carinii* (PCP), for inhibiting the growth of malign tumors, blood pressure reduction, neuroprotection, and for combating viral infections such as influenza and HIV infections.

The listings above are merely exemplary, and the invention basically encompasses any active agents, which have at least one amidine function or guanidine function that has been transferred according to the invention into an improved prodrug. The method according to the invention is thus applicable to a very wide range of substance classes and indications and is capable of distinctly increasing the bioavailability of many medicinal substances, the active form of which contains an amidine or a guanidine.

As examples for compounds modified according to the method according to the invention, valbenzamidoxime, pentamidine valine ester and diminazene valine ester can be mentioned.

The preparation and use according to the invention is explained in more detail by means of exemplary embodiments, which are in no way intended to limit the scope of the present invention.

Exemplary Embodiments

Material and Methods

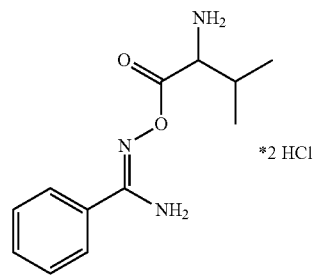 [SMILES: CC(C)C(N)C(=O)O/N=C(\N)c1ccccc1]

valbenzamidoxime 1.21 g of benzamidoxime was dissolved in dried acetonitrile. After addition of 2.604 g of tert-butoxycarbonyl valine, 154 mg of 4-dimethyl aminopyridine and 2.988 g of dicyclohexyl carbodiimide, the mixture was stirred at room temperature for three days. The completeness of the reaction was checked by means of DC.

The solvent was withdrawn and the raw product caused to crystallize from a mixture of ethanol/water (3/1, V/V).

Yield: 86%

Melting point: 147° C.

IR (KBr):

$V=3496, 2928, 2850, 1744, 1686, 1612, 1392, 1374\ cm^{-1}$.

$^1$H-NMR (300 MHz, DMSO-$d_6$):

$\delta$/ppm (TMS)=0.83 (d, 6H, $^3J$=6.4 Hz, CH(CH$_3$)$_2$), 1.40 (s, 9H, C(CH$_3$)$_3$), 2.08 (m, 1H, CH(CH$_3$)$_2$), 4.05 (t, 1H, $^3J$=8.0 Hz, CH—NH), 6.85 (s, 2H, NH$_2$), 7.31 (d, 1H, $^3J$=9.2 Hz, NH), 7.44 (m, 3H, Ar—H), 7.52 (m, 2H, Ar—H).

$^{13}$C-NMR (75 MHz, DMSO-$d_6$):

$\delta$/ppm (TMS)=18.25 (CH$_3$), 18.96 (CH$_3$), 28.15 (C(CH$_3$)$_3$), 30.13 (CH(CH$_3$)$_2$), 59.09 (CH—NH), 78.29 (C(CH$_3$)$_3$), 126.68 ($C_{Ar}$ 2.6), 128.30 ($C_{Ar}$ 3.5), 130.46 ($C_{Ar}$ 1), 131.44 ($C_{Ar}$ 4), 155.73 (C=N), 156.96 (C=O), 168.88 (C=O).

MS (ESI):

m/z (%)=693 [2M+Na$^+$] (15), 336 [M+H$^+$] (100), 280 [M—(CH$_3$)$_2$C=CH$_2$+H$^+$] (44), 137 [BAO+H$^+$] (31), 119 [Val+H$^+$] (5).

$C_{17}H_{25}N_3O_4$ (335.41):

| Ber. | N 12.54% | C 60.90% | H 7.51% |
| Gef. | N 12.63% | C 60.96% | H 7.71% |

For splitting-off the protecting group, 300 mg of the bocvalbenzamidoxime was dissolved in dioxane. HCl gas was introduced over a period of five minutes and stirred overnight. The free ester was precipitated by adding cold ethyl acetate and subsequently washed several times with ether.

Yield: 30%

IR (KBr):

$V=3238, 3052, 2910, 2744, 1800, 1682, 1600, 1374\ cm^{-1}$.

$^1$H-NMR (300 MHz, DMSO-d$_6$):

δ/ppm (TMS)=1.02 (d, 3H, $^3$J=4.7 Hz, CH$_3$), 1.04 (d, 3H, $^3$J=4.7 Hz, CH$_3$), 2.02 (m, 1H, CH(CH$_3$)$_2$), 3.94 (t, 1H, $^3$J=5.4 Hz, CH—NH$_2$), 7.22 (s, 2H, NH$_2$), 7.48 (m, 3H, Ar—H), 7.72 (m, 2H, Ar—H), 8.80 (s, 3H, NH$_3$), 9.03 (s, 1H, NH).

$^{13}$C-NMR (75 MHz, DMSO-d$_6$):

δ/ppm (TMS)=18.07 (CH$_3$(CH$_3$)$_2$), 29.38 (CH(CH$_3$)$_2$), 57.24 (CH—NH$_2$), 126.77 (C$_{Ar}$ 2.6), 128.33 (C$_{Ar}$ 3.5), 130.62 (C$_{Ar}$ 1), 130.09 (C$_{Ar}$ 4), 157.62 (C=N). 165.40 (C=O).

MS (ESI):

m/z (%)=493 [2M+Na$^+$] (43), 471 [2M+H$^+$] (42), 236 [M+H$^+$] (100), 137 [BAO+H$^+$] (68), 121 [BA+H$^+$] (20), 119 [BAO—H$_2$O+H$^+$] (38), 118 [Val+H$^+$] (49).

C$_{12}$H$_{19}$N$_3$O$_2$Cl$_2$ (308.21):

| Ber. | C 46.76% | H 6.21% | N 13.63% |
| Gef. | C 46.54% | H 6.25% | N 13.12% |

For proving the resorption from the gastrointestinal tract and the subsequent reduction to benzamidine, the valbenamidoxime is orally administered to three rats. The metabolization of the ester into benzamidine in this case takes place in vivo as follows:

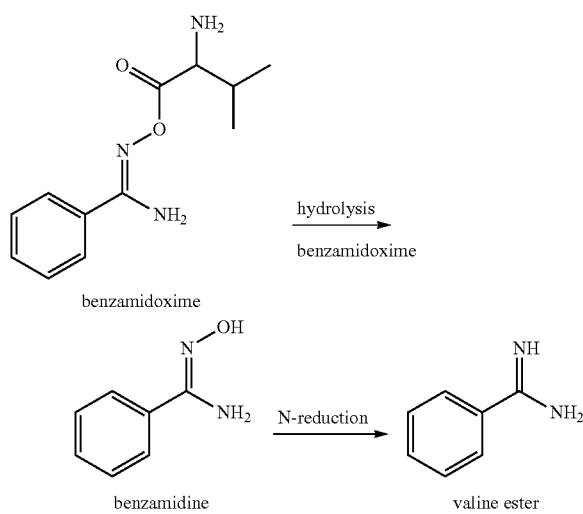

Methods Related to the Execution of the Study with Rats

The animal study was permitted by the Schleswig-Holstein Ministry of Agriculture, Environment and Rural Spaces on Jul. 4, 2007.

The anaesthesia was carried out using xylazine and ketamine. Both were administered by intramuscular injection. The silicone catheters were implanted in the vena jugularis and the arteria carotis. They have locally antithrombotic and anti-inflammatory properties, but are not systemically active. During the surgery, the eyes were protected with a cornea-protective ointment (Oculotect®), and 3-4 ml of Ringer lactate solution was applied subcutaneously for improving the postoperative energy supply. The animals were treated antiphlogistically (Finadyne®, 1 mg/kg of body weight) and antibiotically (Amoxicillin® 15%, 10 mg/kg of body weight) and postoperatively attended and kept warm until they woke up. The day after the surgery, the animals got Nutri Plus®, an energy paste (soy bean oil, molasses, cod-liver oil, meat extract, mineral premixture, vitamin premixture).

After the test was completed, the animals were euthanized using pentobarbital (i.v.).

Keeping of the Rats

Male Wistar rats having an average weight of 200 g served as the test animals. The animals were kept individually in cages. Every second day they got concentrated food. Water and dry food was available ad libitum.

Application of the Substances

For being able to determine the accurate dosage of the substances, the animals were weighed the evening before the substance application. The substances (prodrugs) to be administered orally were applied via a stomach tube. For this purpose, valbenzamidoxime was solved in 100 mM phosphate buffer, pH 6.5. The intravenously administered benzamidine was solved in 0.9% NaCl solution, so as to prevent haemolysis. After the injection, rerinsing with at least 0.5 ml of 0.9% NaCl solution was carried out. The substance application in each case took place in the morning.

The prodrugs were administered to three rats. Benzamidine was applied intravenously to two rats. The orally administered doses of valbenzamidoxime were 50 mg/kg of body weight. Benzamidine was applied in a concentration of 10 mg/kg of body weight.

Blood Sampling

Six blood samples can be taken from one rat. The test period for one condition is one day. The blood samples were obtained over a period of eight hours after oral application, respectively six hours after intravenous application. After the oral administration, the sampling took place after 30, 60, 90, 120, 240 and 480 minutes, after intravenous application after 5, 10, 20, 40, 80 and 360 minutes. Prior to the blood withdrawal, the catheter was emptied by a short aspiration until blood appeared. The blood withdrawal (300 µl) was carried out by means of Multivetten (Multivetten® 600, Sahrstedt, Nümbrecht). For keeping the catheter clear, about 0.3 ml of a mixture of heparin and NaCl were subsequently injected. The obtained full blood was centrifuged (1500 g, 10 min, 4° C.). After the centrifugation, about 150 µl plasma was taken as a supernatant, pipetted into Eppendorf cups and frozen at −80° C.

Reprocessing of the Blood Samples

After slowly defrosting, 150 µl of plasma was diluted with Aqua bidest. ad 600 µl. The plasma samples were subsequently reprocessed by means of solid phase extraction. After conditioning the column with 1000 µl of methanol and equilibrating with 1000 µl of Aqua bidest., the sample application (600 µl) was carried out. The sorbent was washed after the sample application with 600 µl of Aqua bidest. The elution of the substances was carried out by means of Aqua bidest., pH 3/methanol (6/4, V/V). Thereupon, the eluate is concentrated to dryness and absorbed with 100 µl of Aqua bidest./methanol (9/1, V/V) and transferred to the HPLC.

HPLC Analysis for Separating Benzamidoxime and Benzamidine

For separating the substances to be analyzed, the following HPLC method was used:

| HPLC pump: | Waters 600 |
| Detector: | Waters 2417 Tunable Absorbance Detector |
| Autosampler: | Waters 717 plus Autosampler |
| Integrator: | EZChrom ™ Elite Client/Server Version 2.8.3 Build 2249 recording and evaluation software |
| stationary phase: | Synergy Max-RP 80A; 250* 4.6 mm with precolumn C 18 4.0* 3.0 mm (Phenomenex, Aschaffenburg) |

| Column temperature: | 24° C. constant, by means of column heater |
| --- | --- |
| Mobile phase: | 10 mM of octyl sulfonate in Aqua bidest., pH 2.5 (with conc. $H_3PO_4$)/acetonitrile (82.5/17.5, V/V) |
| Run time: | 30 minutes |
| Detection: | UV detector, 229 nm |
| Flow rate: | 1.0 ml/min |
| Injection volume: | 10 μl |
| Detector sensitivity: | absorbance units fullscale: 2,000 |
| Retention times: | benzamidoxime: 23.5 ± 0.5 min |
| | benzamidine: 26.5 ± 0.5 min |

The eluant was filtered using a Satorius membrane filter (0.45 μm) and degassed in an ultrasonic bath for 15 minutes.

HPLC Analysis for Analyzing the Valbenzamidoxime, Benzamidoxime and Benzamidine

For separating the substances to be analyzed, the following HPLC method was used:

| HPLC pump: | Waters 600 |
| --- | --- |
| Detector: | Waters 2417 Tunable Absorbance Detector |
| Autosampler: | Waters 717 plus Autosampler |
| Integrator: | EZChrom ™ Elite Client/Server Version 2.8.3 Build 2249 recording and evaluation software |
| stationary phase: | RP Select B with precolumn 4 * 4 (Merck KgaA, Darmstadt) |
| Mobile phase: | A: 25 mM ammonium acetate in Aqua bidest., pH 6.3/acetonitrile (92.5/7.5, V/V) |
| | B: acetonitrile |

| time [min] | A [%] | B [%] |
| --- | --- | --- |
| 0-15 | 100 | 0 |
| 15-35 | 80 | 20 |
| 35-48 | 100 | 0 |

| Run time: | 48 minutes |
| --- | --- |
| Detection: | 229 nm |
| Flow rate: | 1.0 ml/min |
| Injection volume: | 10 μl |
| Detector sensitivity: | absorbance units fullscale: 2,000 |
| Retention times: | benzamidine: 7.5 ± 0.3 min |
| | benzamidoxime: 12.0 ± 0.3 min |
| | valbenzamidoxime: 32.0 ± 0.5 min |

The eluant was filtered using a Satorius membrane filter (0.45 μm) and degassed in an ultrasonic bath for 15 minutes.

The results of the tests are shown in FIG. 1, in which the plasma level curves of benzamidine after oral administration of the valbenzamidoxime are illustrated.

Figure 2:
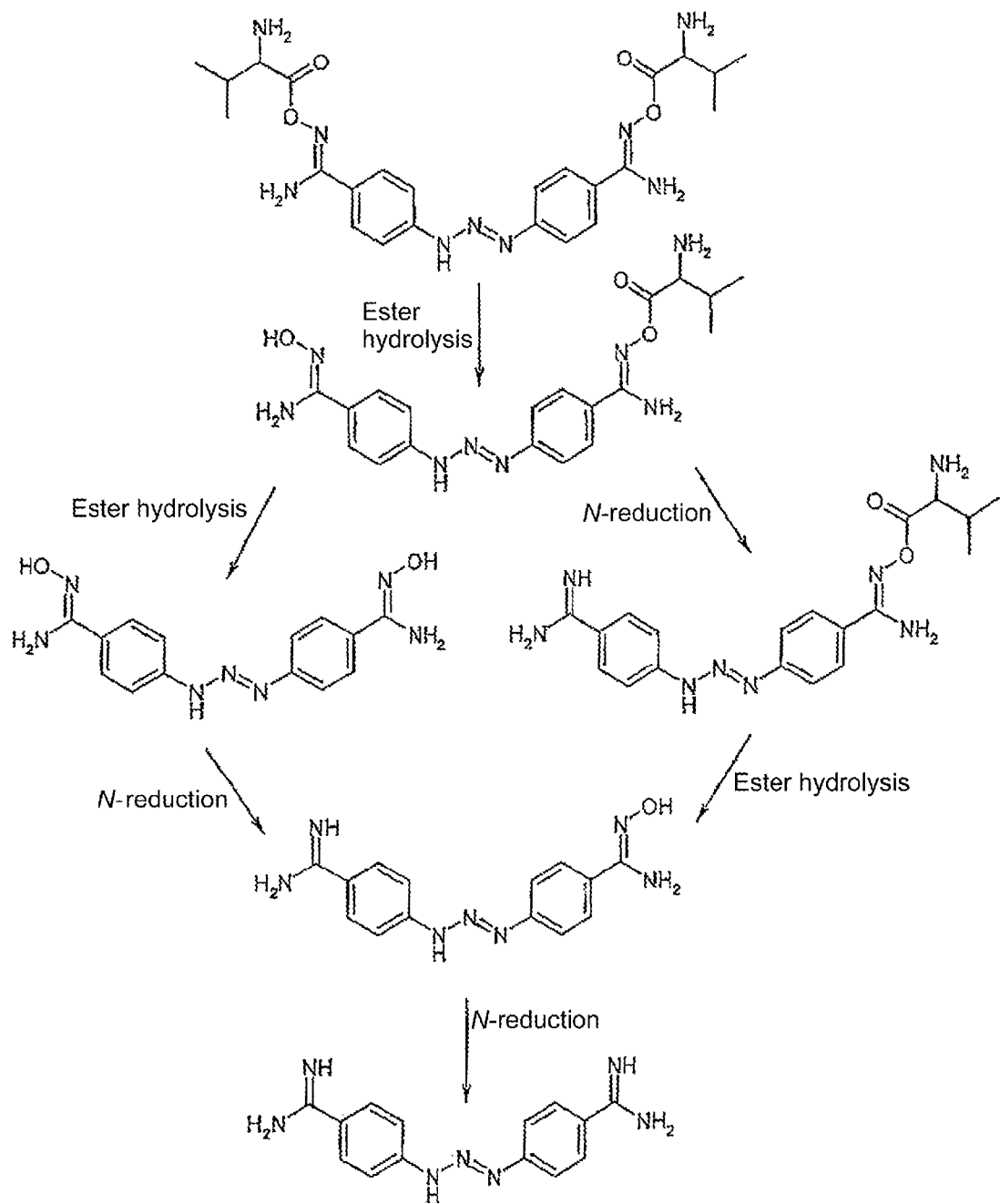
FIG. 2 is a flow chart depicting the metabolism of the diminazene valine ester.
Figure 3:
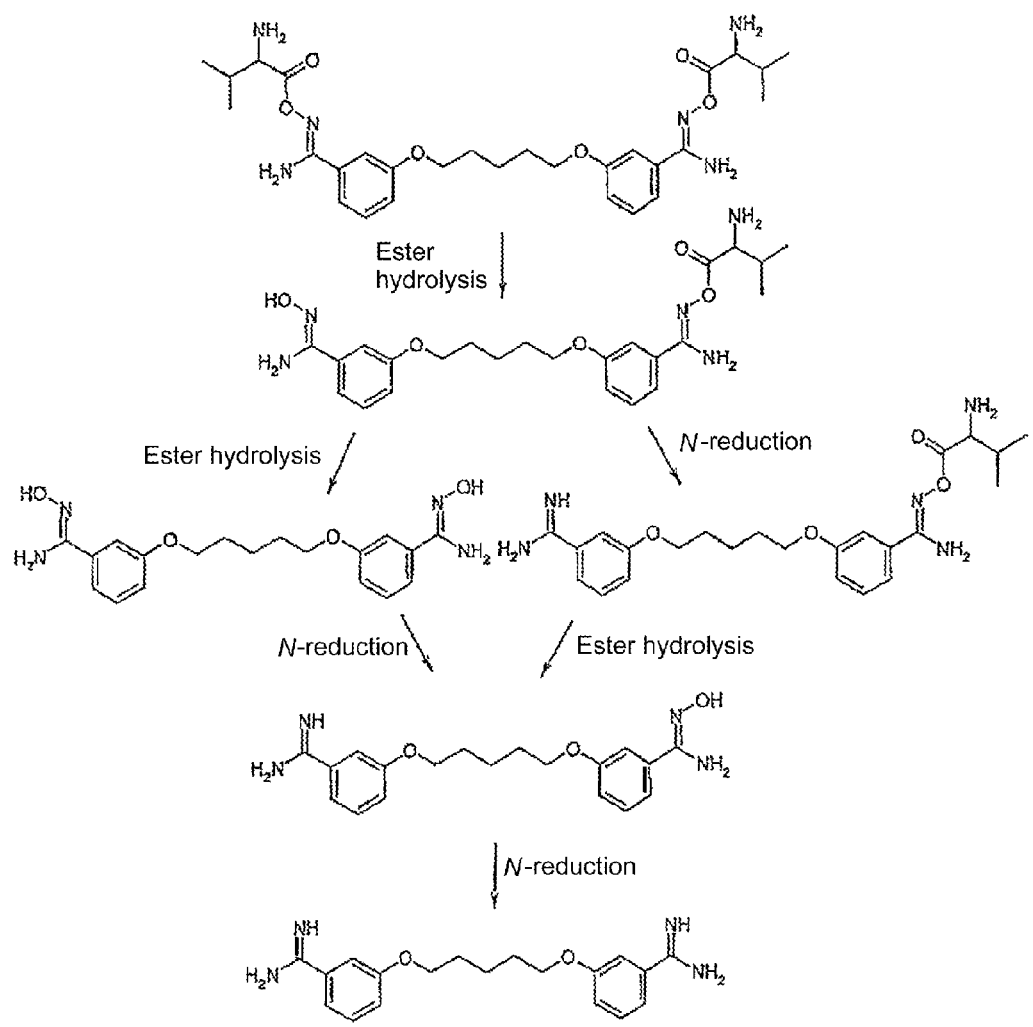
FIG. 3 is a flow chart depicting the metabolism of the pentamidine valine ester.

The metabolism of the diminazene valine ester is illustrated in the flowchart in FIG. 2, and the metabolism of the pentamidine valine ester in the flowchart in FIG. 3.

The oral bioavailability of the benzamidine after oral administration of the valbenzamidoxime could be determined from the obtained data (Table 1):

TABLE 1

| | bioavailability of the benzamidine after oral administration of valbenzamidoxime | | |
| --- | --- | --- | --- |
| | bioavailability [%] | mean value [%] | standard deviation [%] |
| Rat 10 | 111.8 | 87.7 | 27.0 |
| Rat 11 | 74.5 | | |
| Rat 12 | 69.8 | | |

As can be seen from the Table above, benzamidine has a bioavailability of 88% after oral administration of the valbenzamidoxime. This demonstrates that the prodrug was completely resorbed after oral administration and metabolized into the active form benzamidine.

Particular embodiments of the invention are:

1. Use of an amidoxime amino acid ester of the formula (I) or an N-hydroxyguanidine amino acid ester of the formula (II) or amidoxime prolinyl ester of the formula (III)

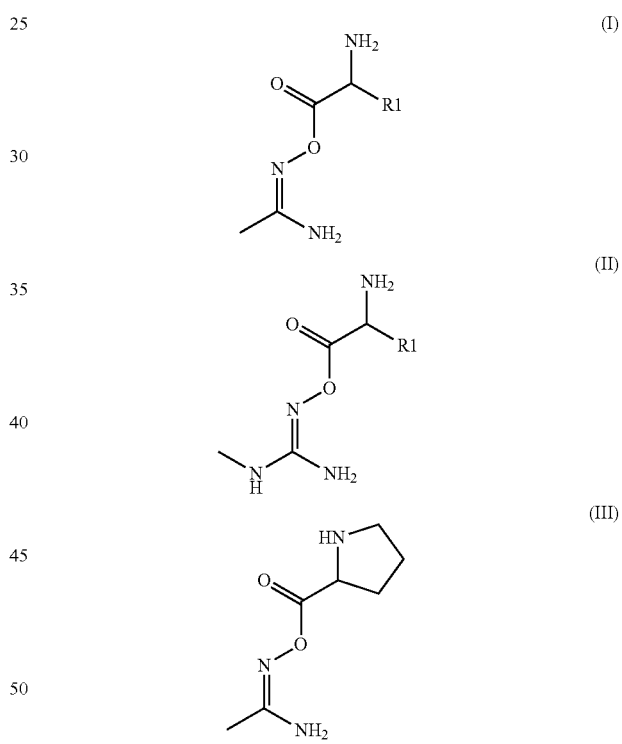

wherein R1 is selected from the group consisting of hydrogen, an alkyl radical, an aryl radical, and one of the groups illustrated in the following

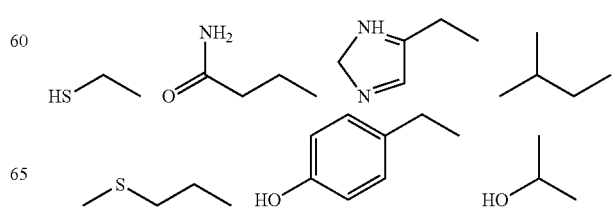

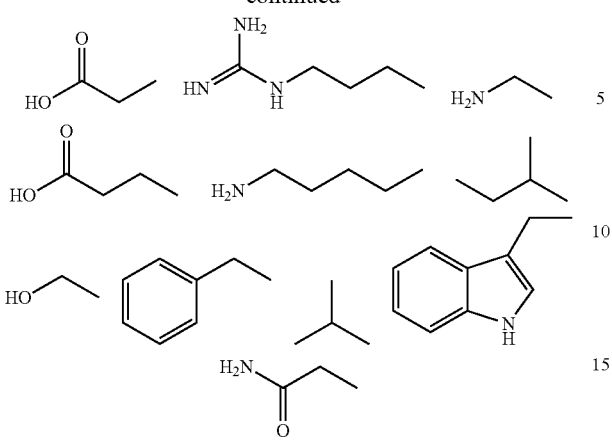

and the salts thereof, as a substitute for one or more amidine functions, N-hydroxyamidine (amidoxime) functions, guanidine functions or N-hydroxyguanidine functions of a medicinal substance in drugs for improving the solubility, bioavailability and/or capacity of the medicinal substance to pass the blood-brain barrier.

2. Use according to embodiment 1, characterized in that the medicinal substance is selected from the group of protease inhibitors, DNA-intercalating and RNA-intercalating compounds, inhibitors of viral enzymes and N-methyl-D-aspartate receptor antagonists.

3. Use according to embodiment 2, characterized in that the protease inhibitor is a thrombin inhibitor, an inhibitor of factor Xa, Factor VII, or of all of the proteases of the coagulation cascade, or a matriptase inhibitor.

4. Use according to embodiment 2, characterized in that the protease inhibitor is an urokinase inhibitor.

5. Use according to embodiment 2, characterized in that the DNA-intercalating or RNA-intercalating compound is pentamidine, diminazene or isometamidium.

6. Use according to embodiment 2, characterized in that the inhibitor of viral enzymes is a neuraminidase inhibitor.

7. Use according to any one of the preceding embodiments, characterized in that the medicinal substance is designed for the prophylaxis and therapy of visceral and/or cutaneous leishmaniasis, trypanosomiasis, the 2nd phase of trypanosomiasis, or pneumonia caused by *pneumocystis carinii*, for inhibiting the growth of malign tumors, for inhibiting blood coagulation, for blood pressure reduction, for neuroprotection, and for combating viral infections including influenza and HIV infections.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of producing a prodrug for a medicinal substance, comprising using a partial structure of formula (I), formula (II) or formula (III),

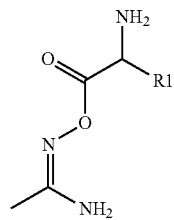

(I)

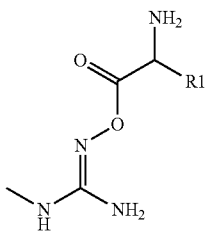

(II)

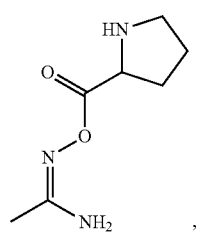

(III)

as a substitute for at least one of an amidine function in the medicinal substance to obtain the prodrug for the medicinal substance, wherein R1 is selected from the group consisting of hydrogen, an alkyl radical, an aryl radical, and one selected from the group consisting of the following:

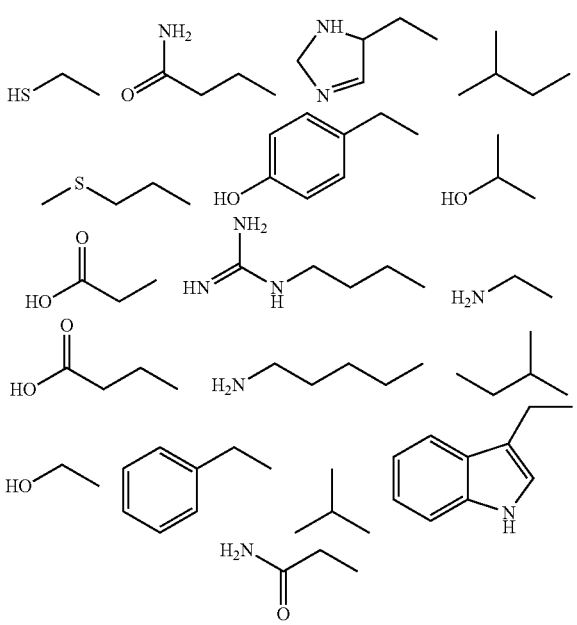

and the salts thereof, wherein the medicinal substance is selected from the group consisting of benzamidine, pentamidine, diminazene, isometamidium and melagatran.

2. The method according to claim 1, wherein the prodrug is selected from the group consisting of valbenzamidoxime, pentamidine valine ester and diminazene valine ester.

3. The method according to claim 1, wherein the overall structure of the prodrug comprises a plurality of at least one of the partial structures of formulas (I), (II) and (III).

4. The method according to claim 1, wherein the medicinal substance is configured for the prophylaxis and therapy of visceral and/or cutaneous leishmaniasis, trypanosomiasis, the $2^{nd}$ phase of trypanosomiasis, or pneumonia caused by *pneumocystis carinii*, for inhibiting the growth of malign tumors, for inhibiting blood coagulation, for blood pressure reduction, for neuroprotection, or for combating viral infections.

5. The method according to claim 1, wherein the prodrug is pentamidine valine ester.

6. A prodrug for a medicinal substance, the prodrug comprising a partial structure having the formula (I), (II) or (III),

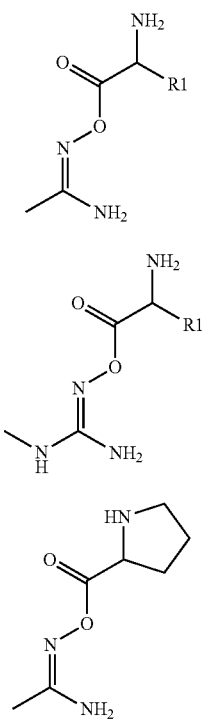

wherein the formula (I), (II) or (III) is used as a substitute for at least one of an amidine function in the medicinal substance, R1 is selected from the group consisting of hydrogen, an alkyl radical, an aryl radical, and one selected from the group consisting of the following:

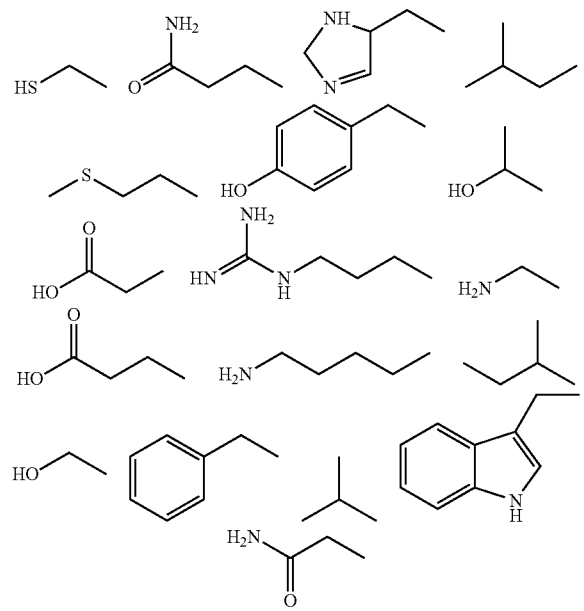

and the salts thereof, and the medicinal substance is selected from the group consisting of benzamidine, pentamidine, diminazene, isometamidium and melagatran.

7. The prodrug according to claim 6, wherein the prodrug is selected from the group consisting of valbenzamidoxime, pentamidine valine ester and diminazene valine ester.

8. The prodrug according to claim 6, wherein the medicinal substance is configured for the prophylaxis and therapy of visceral and/or cutaneous leishmaniasis, trypanosomiasis, the $2^{nd}$ phase of trypanosomiasis, or pneumonia caused by *pneumocystis carinii*, for inhibiting the growth of malign tumors, for inhibiting blood coagulation, for blood pressure reduction, for neuroprotection, or for combating viral infections.

9. The prodrug according to claim 6, wherein the overall structure of the prodrug comprises a plurality of at least one of the partial structures of formulas (I), (II) and (III).

10. The prodrug according to claim 6, wherein the prodrug is pentamidine valine ester.

* * * * *